United States Patent [19]

Reiter

[11] Patent Number: 4,564,699

[45] Date of Patent: Jan. 14, 1986

[54] OXYDEHYDROGENATION PROCESS

[75] Inventor: Stephen E. Reiter, Bartlesville, Okla.

[73] Assignee: Ashland Oil, Inc., Ashland, Ky.

[21] Appl. No.: 379,842

[22] Filed: May 20, 1982

[51] Int. Cl.$^4$ ............................................. C07C 67/317
[52] U.S. Cl. .................................................. 560/214
[58] Field of Search ......................... 560/214; 562/599

[56] References Cited

U.S. PATENT DOCUMENTS

| | | | |
|---|---|---|---|
| 2,026,894 | 1/1936 | Hill | 562/599 |
| 2,376,067 | 5/1945 | Long | 562/599 |
| 3,207,805 | 9/1965 | Gay | 560/214 |
| 3,634,494 | 1/1972 | Tsu | 560/214 |
| 3,639,466 | 2/1972 | Leichtle | 562/599 |
| 3,649,560 | 3/1972 | Croce et al. | 560/214 |
| 3,948,959 | 4/1976 | Cavaterra et al. | 562/599 |

Primary Examiner—Natalie Trousof
Assistant Examiner—L. Hendriksen
Attorney, Agent, or Firm—John F. Jones

[57] ABSTRACT

An isobutyric acid ester is oxidatively dehydrogenated in the vapor phase producing the corresponding methacrylic acid ester by contact with a heterogeneous catalyst, molecular oxygen and an amine. The catalyst may be any of a number of well know oxydehydrogenation catalysts.

5 Claims, No Drawings

_OXYDEHYDROGENATION PROCESS_

BACKGROUND OF THE INVENTION

1. Field of the Invention

This invention relates to an improved method for preparing alkyl methacrylates from alkyl isobutyrates by oxydehydrogenation of the latter over an oxydehydrogenation catalyst in the presence of molecular oxygen wherein an amine is also included in the reaction mixture.

2. Description of the Prior Art

There exists considerable prior art relating to the oxydehydrogenation of the lower saturated aliphatic monocarboxylic acids to produce the corresponding, $\alpha,\beta$-olefinically unsaturated acids. Early work in this area involved thermal, vapor phase oxydehydrogenation of the saturated aliphatic carboxylic acid in the presence of oxygen and iodine. This approach has not been particularly successful from a commercial standpoint. This is understandably so inasmuch as iodine is costly, exhibits extreme corrosivity properties and poses considerable problems in realizing complete recovery of the comparatively large amounts thereof required in the process. The heterogeneous catalytic method for oxydehydrogenation according to the prior art appears to be the more attractive route to the commercial production of $\alpha,\beta$-olefinically unsaturated monocarboxylic acids. The prior art heterogeneous oxydehydrogenation catalysts useful for this purpose include some heteropoly acids, such as phosphomolybdic acid, optionally with tungsten and/or vanadium. Another type of catalyst included in the prior art is iron phosphate.

Iron phosphate subjected to calcination exists in several crystalline phases or species. It is not known at this time which species is or are catalytically active. There is evidence that the presence of certain extrinsic metal components in the catalyst preparation serves to facilitate the formation of the active catalyst. For instance, U.S. Pat. No. 3,948,959 discloses that an alkali or alkaline earth metal can be the extrinsic metal for this purpose. Similarly, other catalysts useful for the oxydehydrogenation reaction are disclosed in U.S. Pat. Nos. 3,917,673; 3,855,279; 4,088,602 and 3,634,494 and elsewhere.

None of the prior art discloses or suggests that the inclusion of an amine in the oxydehydrogenation feed will give much improved conversion and selectivity in the transformation of an isobutyric acid ester to the corresponding methacrylic acid ester.

SUMMARY OF THE INVENTION

In accordance with this invention, an improved catalytic process is provided for the oxidative dehydrogenation of an isobutyric acid ester having the formula:

$$\text{CH}_3 - \underset{\underset{\text{CH}_3}{|}}{\overset{\overset{\text{H}}{|}}{\text{C}}} - \text{COOR}$$

by contacting it with an oxydehydrogenation catalyst in the vapor phase in the presence of molecular oxygen and an amine to produce a methacrylic acid ester having the formula

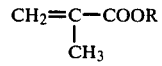

wherein R is an alkyl group having from 1 to 6 carbon atoms and preferably R has from 1 to 4 carbon atoms. Because of present economics and ready availability it is most preferred that R be methyl. The process of this invention comprises contacting an oxydehydrogenation catalyst at a temperature in the range of from 300° to 500° C. with a mixture of the isobutyric acid ester, molecular oxygen and amine. If desired, acetone may also be included in the reaction mixture to give improved yield of the desired methacrylic acid ester. The oxydehydrogenation catalyst can be any of the known catalysts useful for this purpose but the preferred catalyst is an iron phosphate which may contain other elements and also can be on a carrier or support material.

DESCRIPTION OF THE PREFERRED EMBODIMENT

There are several techniques which can be used for preparing the catalysts useful in the process of this invention, for instance, the iron phosphate type. The more facile methods involve preparing the integral catalyst composition prior to calcination. This can be done by the so-called slurry method or the precipitation method. In the latter method an aqueous solution of salts of the metals and phosphoric acid is first prepared and is then neutralized with an appropriate base so as to precipitate the mixed metal phosphates. The precipitate is washed and dried prior to calcination. In the alternative, one can add ammonium phosphate to a solution of the metal salts causing direct precipitation of the metal phosphates. As indicated, any water-soluble salt of iron can be used. The nitrate salts are suitable water-soluble salts for this purpose and are preferred because of their ready availability and desirable solubility characteristics.

The so-called slurry method is the preferred catalyst preparation method because of its convenience. In accordance with this procedure the aqueous solution of the iron and other metals, if desired, together with the phosphoric acid is obtained as previously noted. The solution is then heated with stirring to remove water and this is continued until the mass is so thick that is cannot be stirred. The resulting residue is then broken up and heated to a moderately elevated temperature on the order of about 120° C. until the mass is completely dried. The resulting solid is sized and calcined. Suitable calcination temperatures range from 400°–1000° C. Applicable periods of calcination range from 2 to 30 hours or more.

The use of a support or carrier for the catalysts is included in this invention. The support can be included during the preparation of the catalyst. Suitable carrier materials include silica, alumina, quartz, titania, zirconia, carbon, diatomaceous earth, silicon carbide, etc.

The process of this invention can be carried out using the catalyst in the form of a fluidized bed reactor, a stirred tank reactor or a fixed bed or packed bed reactor or any combination of these types of reactor configurations. Because of the convenience associated with the use of a fixed bed reactor in a small scale operation, such a reactor will be exemplified herein. In the preferred mode of operation the feed to the reactor comprises a pre-heated gaseous mixture of the isobutyric acid ester, molecular oxygen, inert diluent, amine and optionally acetone. A pre-heat temperature in the range of about 300° to 350° C. is customarily used. The oxydehydrogenation reaction can be carried out in the range of from about 300° to 500° C. More preferred is the range of from about 375° to 475° C.

The mole ratio of molecular oxygen to isobutyric acid ester is from 0.5 to 1.5 and more preferably from 0.7 to 0.75 in the case in which the ester is methyl isobutyrate.

The role of the amine in the feed is not known except that its presence surprisingly increases conversion and selectivity to the desired methacrylic acid ester and decreases the undesirable formation of methacrylic acid and other unwanted by-products of the reaction. The mole ratio of the amine to the isobutyric acid ester in the feed should be in the range of from about 0.0001 to 0.05, and more preferably from about 0.0005 to 0.02.

The process of this invention can be represented by the following equation:

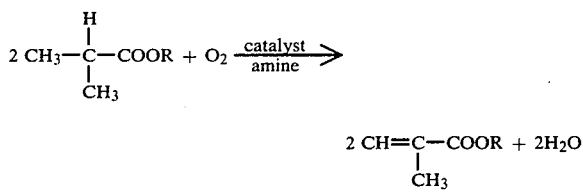

The amine can be any primary, secondary or tertiary organic amine which contains a basic nitrogen atom. Amines useful in this invention include primary amines such as methyl amine, ethyl amine, the propyl amines, the butyl amines, the amyl amines, the hexyl amines, cyclohexyl amines, aniline, other aromatic primary amines; secondary amines include dimethyl amine, diethyl amine, the dipropyl amines, the dibutyl amines, the dihexyl amines, dicyclohexyl amine, methyl ethyl amine, ethyl propyl amine, N-methyl aniline and the like; tertiary amines include trimethyl amine, triethyl amine, the tripropyl amines, the tributyl amines, the trihexyl amines, N,N-dimethyl aniline, pyridine, and ammonia, itself, and the like. It is preferred to use an amine which exists in the vapor state under the oxydehydrogenation conditions outlined above.

Another important parameter is the concentration of the isobutyric acid ester in the feed. This reactant should be present in the feed in from 0.1 to 20 mole percent.

From the standpoint of achieving a reasonable throughput combined with an acceptable yield, the concentration of the isobutyric acid ester in the feed is about 3-6 mole percent. The concentration of the ester is controlled to a large degree by the amount of inert gas present. The preferred inert gas or diluent is nitrogen although other inert gases such as carbon dioxide, helium, argon, and the like are suitable. Air is a very convenient source of oxygen plus inert diluent.

Another important parameter is contact time in the process of this invention. Contact time or reaction time is defined for the purpose of this invention as the catalyst volume divided by the volume of the gas feed per second at the reaction temperature. The catalyst volume is the bulk volume occupied by the catalyst in the reactor. The term catalyst in this sense not only includes the active components of the catalyst, per se, but also includes the support if present. Accordingly, reaction times can range from 0.05 to 3.0 seconds and more preferably in the order of from 0.1 to 1.0 second. The reaction is preferably carried out at or near atmospheric pressure although the use of higher pressures of up to about 10 atmospheres is within the scope of the invention.

The process of this invention is further illustrated in the following specific examples.

EXAMPLE I

An iron phosphate catalyst having the empirical formula $Fe_1P_{1.1-1.2}O_{4.4-4.8}$ which was prepared according to the procedure outlined in U.S. Pat. No. 3,948,959 and having been calcined at 450° C. for 4-6 hours was used in this example to oxydehydrogenate methyl isobutyrate to methyl methacrylate in a steel tube of ½″ O.D. (⅜″ I.D.) and approximately 18″ in length containing 15 cc of the packed catalyst. The gaseous feed was first passed through a preheater made of a stainless steel tube similar to the reactor but packed with glass beads. The condensed organic product from the reactor was collected and analyzed by the internal standard method of gas chromatography.

The mole ratio of methyl methacrylate to methacrylic acid in the product was determined. The feed to the reactor consisted of methyl isobutyrate:oxygen:nitrogen in the mole ratio of 1:0.5-1:30-60, respectively. The reaction temperature was 400° C. and the contact time was 0.3 seconds. The mole ratio of methyl methacrylate to methacrylic acid varied between 0.5 and 0.8. This experiment, which is outside the scope of the present invention, shows that the major portion of the oxydehydrogenation product is always methacrylic acid in the prior art process.

EXAMPLE II

The procedure of Example I was repeated except that two mole percent of pyridine based on the mole percent of the methyl isobutyrate was included in the feed. It was found that the mole ratio of methyl methacrylate to methacrylic acid in the product was from 5 to 12. Thus, the use of pyridine in the oxydehydrogenation increases the production of methyl methacrylate relative to methacrylic acid at least about five fold over the process of the prior art.

EXAMPLE II

The procedure of Example I was repeated except that two mole percent of N-butyl amine was included in the feed. It was found that the mole ratio of methyl methacrylate to methacrylic acid in the product was in the range of 8-13. Thus, the use of butyl amine in the feed enhances the formation of methyl methacrylate relative to methacrylic acid many fold over the prior art processes.

I claim:

1. In a process for the catalytic conversion of an isobutyric acid ester to a methacrylic acid ester by oxydehydrogenation wherein an iron phosphate type of oxydehydrogenation catalyst is contacted with a gaseous stream containing said isobutyric ester and molecular oxygen at a temperature of from about 300° C. to 500° C.; the improvement comprising including in the gaseous stream an amine selected from the group consisting of butyl amine and pyridine whereby the converion and selectivity to the desired methacrylic acid ester is increased and the undesirable formation of methacrylic acid is decreased.
2. The process of claim 1 wherein the isobutyric acid ester has the formula
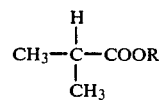
wherein R is an alkyl group having from 1-6 carbon atoms.
3. The process of claim 2 wherein R is a methyl group.
4. The process of claim 3 wherein the amine is butyl amine.
5. The process of claim 3 wherein the amine is pyridine.